(12) United States Patent
Texier-Nogues et al.

(10) Patent No.: US 9,180,210 B2
(45) Date of Patent: *Nov. 10, 2015

(54) NANOCRYSTAL NANO-EMULSION

(75) Inventors: Isabelle Texier-Nogues, Grenoble (FR); Toufic Daou, Mulhouse (FR); Mathieu Goutayer, Saint Malo (FR)

(73) Assignee: COMMISSARIAT A L'ENERGIE ATOMIQUE ET AUX ENERGIES ALTERNATIVES, Paris (FR)

( * ) Notice: Subject to any disclaimer, the term of this patent is extended or adjusted under 35 U.S.C. 154(b) by 442 days.

This patent is subject to a terminal disclaimer.

(21) Appl. No.: 13/058,849

(22) PCT Filed: Aug. 14, 2009

(86) PCT No.: PCT/EP2009/060534
§ 371 (c)(1),
(2), (4) Date: Jul. 28, 2011

(87) PCT Pub. No.: WO2010/018222
PCT Pub. Date: Feb. 18, 2010

(65) Prior Publication Data
US 2011/0274622 A1    Nov. 10, 2011

(30) Foreign Application Priority Data
Aug. 14, 2008    (FR) ...................................... 08 55588

(51) Int. Cl.
| A61K 49/00 | (2006.01) |
| A61K 47/44 | (2006.01) |
| A61K 9/00  | (2006.01) |
| A61K 9/107 | (2006.01) |
| A61K 41/00 | (2006.01) |
| A61K 47/10 | (2006.01) |
| A61K 47/14 | (2006.01) |
| A61K 47/24 | (2006.01) |

(52) U.S. Cl.
CPC ........... *A61K 49/0067* (2013.01); *A61K 9/0019* (2013.01); *A61K 9/1075* (2013.01); *A61K 41/0052* (2013.01); *A61K 47/10* (2013.01); *A61K 47/14* (2013.01); *A61K 47/24* (2013.01); *A61K 47/44* (2013.01); *A61K 49/0078* (2013.01)

(58) Field of Classification Search
None
See application file for complete search history.

(56) References Cited

U.S. PATENT DOCUMENTS

| 4,906,100 A | 3/1990 | Rice et al. |
| 5,098,606 A | 3/1992 | Nakajima et al. |
| 5,152,923 A | 10/1992 | Weder et al. |
| 5,403,575 A | 4/1995 | Kaufman et al. |
| 5,464,696 A | 11/1995 | Tournier et al. |
| 5,472,706 A | 12/1995 | Friedman et al. |
| 5,665,687 A | 9/1997 | Khayat et al. |
| 5,976,502 A | 11/1999 | Khoobehi et al. |
| 6,113,921 A | 9/2000 | Friedman et al. |
| 6,123,923 A | 9/2000 | Unger et al. |
| 6,350,431 B1 | 2/2002 | Snow et al. |
| 6,541,018 B1 | 4/2003 | Simmonet et al. |
| 6,559,183 B1 | 5/2003 | Schmid et al. |
| 6,949,257 B2 | 9/2005 | Lang et al. |
| 7,014,839 B2 | 3/2006 | Klaveness et al. |
| 8,557,861 B2 | 10/2013 | Chen |
| 2002/0015721 A1 | 2/2002 | Simmonet et al. |
| 2002/0102301 A1 | 8/2002 | Schwarz |
| 2003/0152635 A1 | 8/2003 | Heurtault et al. |
| 2003/0157021 A1 | 8/2003 | Klaveness et al. |
| 2004/0092428 A1* | 5/2004 | Chen et al. .......................... 514/2 |
| 2005/0079131 A1* | 4/2005 | Lanza et al. .................. 424/1.11 |
| 2005/0129639 A1 | 6/2005 | Quemin |
| 2005/0180997 A1 | 8/2005 | Benita et al. |
| 2005/0255044 A1 | 11/2005 | Lomnes et al. |
| 2006/0222716 A1 | 10/2006 | Schwarz et al. |
| 2006/0257493 A1 | 11/2006 | Amiji et al. |
| 2007/0053988 A1 | 3/2007 | Royere et al. |
| 2007/0092447 A1 | 4/2007 | Padilla de Jesus et al. |
| 2007/0148194 A1 | 6/2007 | Amiji et al. |
| 2010/0144899 A1* | 6/2010 | Goutayer et al. .......... 514/772.1 |
| 2010/0284932 A1 | 11/2010 | Goutayer et al. |
| 2011/0195029 A1 | 8/2011 | Guyon et al. |
| 2011/0200532 A1 | 8/2011 | Goutayer et al. |
| 2011/0201695 A1 | 8/2011 | Mourier-Robert et al. |

FOREIGN PATENT DOCUMENTS

| CN | 1676125 A | 10/2005 |
| EP | 0211258 A2 | 2/1987 |
| EP | 0406162 A  | 1/1991 |
| EP | 0429248 A2 | 5/1991 |

(Continued)

OTHER PUBLICATIONS

Liu et al. Preparation and characterization of novel fluorescent nanocomposite particles: CdSe/ZnS core-shell quantum dots loaded solid lipid nanoparticles. 2008 J. Biomed. Mater. Res. A. 84: 1018-1025. Published online Aug. 1, 2007.*

(Continued)

*Primary Examiner* — Michael G Hartley
*Assistant Examiner* — Jennifer Lamberski
(74) *Attorney, Agent, or Firm* — Nicolas E. Seckel

(57) ABSTRACT

A nanocrystal formulation in the form of a nano-emulsion includes a continuous aqueous phase and at least one dispersed oily phase, in which the oily phase has at least one amphiphilic lipid and at least one solubilising lipid, and in which the aqueous phase has a cosurfactant. The invention also relates to a method for the production of the formulation as well as uses within the fields of medical imaging, thermotherapy or phototherapy.

7 Claims, 5 Drawing Sheets

(56) References Cited

FOREIGN PATENT DOCUMENTS

| EP | 1010416 A | 6/2000 |
|---|---|---|
| EP | 1018363 A | 7/2000 |
| EP | 1693445 A1 | 8/2006 |
| GB | 2251381 A | 7/1992 |
| JP | 62-29511 A | 2/1987 |
| JP | 03-47527 A | 2/1991 |
| JP | 03-161430 A | 7/1991 |
| JP | 04-504108 A | 7/1992 |
| JP | 07-503976 A | 4/1995 |
| JP | 08-157325 A | 6/1996 |
| JP | 08-506081 A | 7/1996 |
| JP | 08-507515 A | 8/1996 |
| JP | 2001-519396 A | 10/2001 |
| JP | 2001-526650 A | 12/2001 |
| JP | 2006-008700 A | 1/2006 |
| JP | 2006-223306 A | 8/2006 |
| JP | 2008-514720 A | 5/2008 |
| WO | 90/06746 A1 | 6/1990 |
| WO | 9312766 A | 7/1993 |
| WO | 93/18752 A1 | 9/1993 |
| WO | 94/04197 A1 | 3/1994 |
| WO | 94/20072 A1 | 9/1994 |
| WO | 9848845 A | 11/1998 |
| WO | 9857666 A | 12/1998 |
| WO | 99/18967 A1 | 4/1999 |
| WO | 0028971 A | 5/2000 |
| WO | 0164328 A | 9/2001 |
| WO | 2005077422 A2 | 8/2005 |
| WO | 2006/037089 A2 | 4/2006 |
| WO | 2006087156 A1 | 8/2006 |
| WO | 2006102768 A1 | 10/2006 |
| WO | 2008102065 A1 | 8/2008 |
| WO | 2008125747 A2 | 10/2008 |

OTHER PUBLICATIONS

Suppocire.TM. Standard product information. 2010 Gattefosse website <http://www.gattefosse.com/en/applications/?administration-route,rectal-vaginal,standard>. Accessed Aug. 9, 2012.*
Entry for "lecithin". 2005 Stedman's Medical Dictionary. Lippincott Williams & Wilkins, 28th Edition.*
Hsu et al. Behavior of soybean oil-in-water emulsion stabilized by nonionic surfactant. 2003 J. Colloid Interface Sci. 259: 374-381.*
Liu et al., "A new bioimaging carrier for fluorescent quantum dots: Phospholipid nanoemulsion mimicking natural lipoprotein core", Drug Delivery: Journal of Delivery and Targeting of Therapeutic Agents, vol. 13, No. 2, pp. 159-164 (2006).
Primo et al.: "Binding and photophysical sudies of biocompatibel magnetic fluid in biological medium and development of magnetic nanoemulsion: A new candidate for cancer treatment", Journal of Magnetism and Magnetic Materials, Elsevier Science Publishers, Amsterdam, NL, vol. 310, No. 2, pp. 2838-2840 (2007).
2007 AAPS Annual Meeting & Exposition—Sasol Olefins & Surfactants Product Brochure, Nov. 10-15, 2007, http://abstracts.aapspharmaceutica.com/ExpoAAPS07/Data/EC/Event?Exhibitors/e62/cb63fb76-28f4-4948-a6d0-ae249dae9c30.pdf (retrieved Mar. 12, 2009).
Chung et al., "Stability of the Oil-in-Water Type Triacylgyceral Emulsions," Biotechnology and Bioprocess Engineering, vol. 6, pp. 284-288 (2001).
Goutayer et al., "Organic Nano-Particles for Non-Invasive Fluorescence Imaging in Mice," Bulletin du Cancer (Montrouge), vol. 95, No. Sp. Iss. SI, pp. S21-S22.
International Search Report (ISR) in PCT/EP2009/060534 mailed Dec. 22, 2009.
Bai et al.: "A versatile bottom-up assembly approach to colloidal spheres from nanocrystals," Angewandte Chemie International Edition Wiley-Vch Verlag GmbH, Germany, vol. 46, No. 35, pp. 6650-6653 (2007).
Akkar et al.: "Formulation of intravenous Carbamazepine emulsions by SolEmuls<(>R) technology," European Journal of Pharmaceutics and Biopharmaceutics, Elsevier Science Publishers B.V., Amsterdam, The Netherlands, vol. 55, No. 3, pp. 305-312 (2003).
Anonymous: "Lipofundin MCT/LCT," B. Braun Melsungen AG Product Information, http://www.gheg.de/media/product/4623/Product_info.pdf (retrieved Mar. 12, 2009).
French search report of priority French Appl. No. 0855588, dated Mar. 12, 2009 (w/ category codes).
Rodriguez et al., "Encapsulation and stabilization of indocyanine green within poly(styrene-alt-maleic anhydride) block-poly(styrene) micelles for near-infrared imaging", J. Biomedical Optics, vol. 13, No. 1, pp. 014025-1 to 014025-10 (Jan.-Feb. 2008); Cited in Japanese counterpart of U.S. Appl. No. 13/058,850.
International Search Report (ISR) mailed Jan. 22, 2009 for International Application No. PCT/FR2008/000196 (WO2008/125747A3), corres. to U.S. Appl. No. 12/527,314.
Kalchenko et al., "Use of lipophilic near-infrared dye in whole-body optical imaging of hematopoietic cell homing", J. of Biomedical Optics, vol. 11, No. 5, Sep. 2006, p. 050507, XP002511213; Cited in ISR of co-pending U.S. Appl. No. 12/527,314.
Primo et al., "Binding and photophysical studies of biocompatible magnetic fluid in biological medium and development of magnetic nanoemulsion: a new candidate for cancer treatment", J. of Magnetism and Magnetic Materials, Elsevier, NL, vol. 310, No. 2, Mar. 2007, pp. 2838-2840, XP002447726; Cited in ISR of co-pending U.S. Appl. No. 12/527,314; Cited in ISR of co-pending U.S. Appl. No. 13/058,850.
Friedlander et al., Involvement of integrins alpha v. beta 3 and alpha v. beta 5 in ocular neovasclar diseases, 1996 Proc. Natl Acad. Sci., USA 93:9764-9769; Cited by Examiner in co-pending U.S. Appl. No. 12/527,314.
International Search Report (ISR) mailed Dec. 22, 2009 for International Application No. PCT/FR2008/050249 (WO2008/104717A3), corres. to U.S. Appl. No. 12/527,371.
Zeevi et al., "The design and characterization of a positively charged submicron emulsion contianing a sunscreen agent", Intl. J. of Pharmaceutics, Elsevier BV, NL, vol. 108, No. 1 (Jan. 1, 1994), pp. 57-68, XP008013777; Cited in ISR of co-pending U.S. Appl. No. 12/527,371.
Mason et al., "Nanoemulsions: formation, structure and physical properties", J. Phys: Condens. Matter, vol. 18, Sep. 29, 2006, pp. R635-R665, XP002502173; Cited in ISR of co-pending U.S. Appl. No. 12/527,371.
International Search Report (ISR) mailed Dec. 22, 2009 for International Application No. PCT/EP2009/060539 (WO2010018223A1), corres. to co-pending U.S. Appl. No. 13/058,850.
Liversidge et al., "Influence of physicochemical interactions on the properties of suppositories," International Journal of Pharmaceutics, Elsevier, BV, NL, vol. 7, No. 3 (1991), Cited in ISR of co-pending U.S. Appl. No. 13/058,850.
Bourdon et al., "A comparative study of the cellular uptake, localization and phototoxicity of meta-tetra(hydroxyphenyl chlorin encapsulated in surface-modified submicronic oil/water carriers in HT29 tumor cells," Journal of Photochemistry and Photobiology, vol. 55, lines 2-3 (2000); Cited in ISR of co-pending U.S. Appl. No. 13/058,850.
Bourdon et al., "Biodistribution of meta-tetra(hydroxyphenyl)chlorin incorproated into surface-modified nanocapsules in tumor-bearing mice," Photochemical and Photobiological Sciences, vol. 1, No. 9, pp. 709-714 (2002); Cited in ISR of co-pending U.S. Appl. No. 13/058,850.
Primo et al., "Photophysical studies and in vitro skin permeation/retention of Foscan/nanoemulsion (NE) applicable to photodynamic therapy skin cancer treatment," Journal of Nanoscience and Nanotechnology, vol. 8, No. 1, pp. 340-347 (2008); Cited in ISR of co-pending U.S. Appl. No. 13/058,850.
Mordon et al., "Selective laser photocoagulation of blood vessels in a hamster skin flap model using a specific ICG formulation," Lasers in Surgery and Medicine, vol. 21, No. 4, pp. 365-373 (1997); Cited in ISR of co-pending U.S. Appl. No. 13/058,850; Cited in ISR of co-pending U.S. Appl. No. 13/058,851.
Reddi, "Role of delivery vehicles for photosensitizers in the photodynamic therapy of tumors," J. of Photochemistry and

(56) References Cited

OTHER PUBLICATIONS

Photobiology, Biology, Elsevier Science, Basel, Switzerland, vol. 37, No. 3, pp. 189-195 (1997); Cited in ISR of co-pending U.S. Appl. No. 13/058,850.

Mehnert et al., "Solid lipid nanoparticles production, characterization and applications," Advanced Drug Delivery Reviews, Elsevier BV, Amsterdam, Netherlands, vol. 47, No. 2/03, pp. 163-196 (2001); Cited in ISR of co-pending U.S. Appl. No. 13/058,850.

Bouchemal et al., "Nano-emulsion formulation using spontaneous emulsification: solvent, oil and surfactant optimisation", Int'l J. of Pharmaceutics 280 (2004) 241-251; Cited by Examiner in co-pending U.S. Appl. No. 13/058,850.

Heurtault et al., "Physico-chemical stability of colloidal lipid particles", Biomaterials 24 (2003) 4283-4300; Cited by Examiner in co-pending U.S. Appl. No. 13/058,850.

International Search Report (ISR) mailed Apr. 20, 2010 for International Application No. PCT/EP2009/060518 (WO2010018216A1), corres. to co-pending U.S. Appl. No. 13/058,851.

Gunstone et al. "Lipid Technologies and Applications", CRC Press, Ed. 1, p. 672 (1997); Cited by Examiner in co-pending U.S. Appl. No. 13/058,851.

International Search Report (ISR) mailed Jan. 15, 2010 for International Application No. PCT/IB2009/006766 (WO2010/018460A1), corres. to U.S. Appl. No. 13/058,984.

Teixeira et al., "Factors Influencing the Oligonucleotides Release From O-W Submicron Cationic Emulsions". Journal of Controlled Release, Elsevier,vol. 70, No. 1/02, pp. 243-255, XP 001197324, ISSN: 0168-3659 (Jan. 29, 2001); Cited in ISR of co-pending U.S. Appl. No. 13/058,984; Cited by Examiner in co-pending U.S. Appl. No. 13/058,984.

Teixiera et al., "Characterization of Oligonucleotide Lipid Interactions in Submicron Cationic Emulsions: Influence of the Cationic Lipid Structure and the Presence of PEG-Lipids", Biophysical Chemistry, vol. 92, No. 3. pp. 169-181, XP001197325, ISSN: 0301-4622, (Sep. 18, 2001); Cited in ISR of co-pending U.S. Appl. No. 13/058,984.

Chattopadhyay et al., "Chemistry and Biology of N-(7-nitrobenz-2-oxa-1,3-diazol-4-yl)-labeled lipids: Fluorescent Probes of Biological and Model Membranes", Review Article, Chemistry and Physics of Lipids, vol. 53, No. 1, pp. 1-15, XP024783533, ISSN: 0009-3084, (Mar. 1, 1990); Cited in ISR of co-pending U.S. Appl. No. 13/058,984.

Chen et al., "Fast Release of Lipophilic Agents From Circulating PEG-PDLLA Micelles Revealed by In Vivo Forster Resonance Energy Transfer Imaging", LANGMUIR, vol. 24, No. 10, pp. 5213-5217, XP002510881, ISSN: 0743-7463, (Aug. 2, 2008); Cited in ISR of co-pending U.S. Appl. No. 13/058,984.

Lundberg, "Preparation of drug-carrier emulsions stabilized with phosphatidylcholine-surfactant mixtures", J. Pharm. Sci., vol. 83, pp. 72-75 (1994); Cited by Examiner in co-pending U.S. Appl. No. 12/527,314.

Weyenberg et al., "Cytotoxicity of submicron emulsions and solid lipid nanoparticles for dermal application", Int'l J. Pharmaceutics, vol. 337, pp. 291-298 (2007); Cited by Examiner in co-pending U.S. Appl. No. 13/058,850.

Jiang et al., "γ-tocopherol, the major form of vitamin E in the US diet, deserves more attention", Am. J. Clin. Nutr. 2001; 74:174-22; cited by Examiner in co-pending U.S. Appl. No. 12/527,371.

\* cited by examiner a.

b.

NANOCRYSTAL NANO-EMULSION

The present invention relates to a nanocrystal formulation in the form of a nano-emulsion, for application within the fields of biology and medicine. The invention also relates to a method for preparing these formulations as well as use, in particular for medical imaging.

JOINT RESEARCH AGREEMENT STATEMENT

This application is for a claimed invention which was made on or on behalf of parties to a Joint Research Agreement (JRA), and as a result of activities undertaken within the scope of the JRA, which was in effect on or before the date the claimed invention was made. Parties to the JRA are:

Commissariat à l'Energie Atomique et aux Energies Alternatives ("CEA"),
Centre National de la Recherche Scientifique ("CNRS"),
Université Pierre et Marie Curie ("Paris 6").

PRIOR ART

Nanocrystals, such as luminescent semiconductor nanocrystals, also known as quantum particles or quantum dots, have significant photochemical and photophysical properties combined with good stability, which means their use is very beneficial within the fields of biology and medicine.

It is therefore proposed to advantageously replace the organic compounds normally used with nanocrystals in numerous applications, such as in particular:

- magnetic resonance imaging (MRI) using iron oxide nanocrystals (Wagner, V., et al., The emerging nanomedicine landscape, Nat. Biotechnol., 2006, 24(10): p. 1211-12171),
- fluorescence imaging and phototherapy using luminescent semiconductor nanocrystals (Azzazy, H. M. E., M. M. H. Mansour, and S. C. Kazmierczak, From diagnostics to therapy: prospects of quantum dots, Clinical Biochemistry, 2007, 40: p. 917-927),
- thermotherapy and/or optical imaging (Loo, C., et al., Immunotargeted nanoshells for integrated cancer imaging and therapy. Nano Lett., 2005, 5(4): p. 709-711) or with X-rays using gold nanocrystals (Kim, D., et al., Antibiofouling polymer-coated gold nanoparticles as a contrast agent for in vivo X-ray computed tomography imaging, J. Am. Chem. Soc., 2007, 129: p. 7661-7665).

These applications generally involve administering nanocrystals to a patient, for example by way of injection. It is thus necessary to provide a formulation of these nanocrystals which is stable and suitable for injection, in particular biocompatible.

After synthesis, the nanocrystals are generally obtained in a form stabilised by organic ligands which makes it possible to control their growth. The nanocrystals may be solubilised in a biocompatible aqueous medium by replacing the ligands with bifunctional ligands having, at one end, an affinity for the nanocrystal surface and, at the other end, an affinity for the aqueous medium.

However, the aqueous formulations obtained are still unstable. In fact, the ligands compete with the other molecules present in the medium and any modification of pH, temperature, or even the presence of oxygen may destabilise the solution and cause the nanocrystals to flocculate. In the case of these nanocrystals, an unwanted non-specific adsorption of proteins or of DNA is also observed. Lastly, the intrinsic properties of the nanocrystals may degenerate in formulations of this type, for example affecting the quantum yield of luminescent semiconductor nanocrystals.

In order to better stabilise the nanocrystals and to preserve their properties, it has been suggested to encapsulate them in different systems, for example in a layer of amphiphilic ligands, an inorganic shell, or even in a bigger nanosystem.

Encapsulation of luminescent semiconductor nanocrystals in lipid micelles is thus described in Schroeder et al., Folate mediated tumor cell uptake of quantum dots entrapped in lipid nanoparticles, J. Control. Release, 2007, 124: p. 28-34. The nanoparticles, called lipodots, are obtained by centrifugation after mixing the constituents in chloroform, evaporation of the solvent and resuspension in water. In this case, the nanoparticle size distribution is very large, ranging from 60 to 200 nm. It is believed that the luminescent semiconductor nanocrystals are, in fact, encapsulated in micelles subsequently forming larger aggregates, which would explain the significant inhibition of fluorescence observed (−98.5%).

Furthermore, S. K. Mandel et al. (Langmuir 2005, 21, 4175-4179) describe the joint encapsulation of iron oxide nanocrystals and fluorescent semiconductor nanocrystals in octane nano-emulsions. However, an emulsion of this type is not biocompatible owing to the presence of octane.

Technical Problem

There is thus a need to provide a nanocrystal formulation which is adapted to specific needs within the fields of biology and medicine, in particular within the field of medical imaging.

More specifically, a formulation which is biocompatible, stable and preserves the intrinsic properties of the nanocrystals is sought.

Lastly, it would be beneficial to provide a formulation enabling targeted in vivo biodistribution towards the region to be imaged or treated.

SUMMARY OF THE INVENTION

According to the invention, it is proposed to encapsulate the nanocrystals in the oily dispersed phase of a nano-emulsion having a specific stable formulation and being prepared using only constituents approved for human injection.

According to a first aspect, the invention also relates to a nanocrystal formulation in the form of a nano-emulsion, comprising a continuous aqueous phase and at least one dispersed oily phase, in which the oily phase comprises at least one amphiphilic lipid and at least one solubilising lipid and in which the aqueous phase comprises a cosurfactant.

The nanocrystals may be formed, in particular, from metals or oxides and may be conductors or semiconductors. The invention relates, in particular, to luminescent nanocrystals.

The amphiphilic lipid is preferably a phospholipid. The solubilising lipid advantageously comprises at least one fatty acid glyceride and preferably at least one saturated fatty acid glyceride comprising 12 to 18 carbon atoms. Furthermore, the oily phase of the nanocrystal formulation may also comprise at least one oil.

The cosurfactant preferably comprises at least one chain formed of ethylene oxide units or ethylene oxide and propylene oxide units. The cosurfactant is advantageously selected from the conjugated compounds polyethylene glycol/phosphatidylethanolamine (PEG/PE), fatty acid and polyethylene glycol ethers and fatty acid and polyethylene glycol esters, and ethylene oxide and propylene oxide block copolymers.

According to one embodiment, the nanocrystal formulation comprises a dispersed phase which is functionalised, for example by grafting the amphiphilic lipid or cosurfactant with a biological ligand.

According to a second aspect, the invention relates to a method for preparing a nanocrystal formulation, comprising at least one continuous aqueous phase and at least one dispersed oily phase, comprising the steps of:
(i) preparing the oily phase comprising at least one solubilising lipid, an amphiphilic lipid and a suitable amount of nanocrystals
(ii) preparing the aqueous phase containing a cosurfactant;
(iii) dispersing the oily phase in an aqueous phase under the effect of sufficient shear force to form a nano-emulsion; and
(iv) recovering the nano-emulsion thus formed.

The shear force effect is preferably produced by sonication. The oily phase is advantageously prepared by placing all or some of the constituents in solution in an appropriate solvent and subsequently evaporating the solvent.

According to a last aspect, the invention relates to the use of nanocrystal formulation according to the invention for medical imaging, thermotherapy or phototherapy.

In particular, the nano-emulsions advantageously exhibit excellent colloidal stability during storage (>3 months) and a good ability to encapsulate nanocrystals as well as an increased concentration in the dispersed phase. During application, a long plasmatic life has also been observed after intravenous injection of the nanoparticles into the organism (stealthy character).

Generally, the nano-emulsion according to the invention is suitable for use within the fields of biology and medicine, in particular by way of injection, since it can be prepared using components approved for human injection.

In this application, the nano-emulsion makes it possible to manage the biodistribution of the nanocrystals by controlling the biodistribution of the nano-emulsion acting as a vector. Rapid recognition of the nanocrystals by the immune system is thus avoided, along with the resultant reduced lifetime in the blood circulation.

The nanoparticles formed by the dispersed phase have a long plasmatic life after intravenous injection. This may result from the low zeta potential of the nano-emulsions. Zeta potential is a parameter which influences the biodistribution of the nano-emulsion, thus upon contact with cells, a positive zeta potential thus encourages endocytosis.

The dispersed phase of the nano-emulsion may easily be functionalised at the surface by biological ligands so as to increasingly target the transportation of the nanocrystals towards the tissues to be imaged or treated.

Owing to an increased concentration of cosurfactant in the continuous aqueous phase, the nano-emulsion also exhibits a dispersed phase having a very small diameter. A nano-emulsion encapsulating nanocrystals having an average diameter of 3 to 12 nm thus typically has an average diameter lower than 50 nm, and preferably between 30 and 40 nm.

The nano-emulsion described advantageously has an increased concentration of the dispersed phase, for example of more than 10%, and in particular 20 to 40% by weight relative to the weight of the nano-emulsion.

Lastly, the proposed nano-emulsion can be obtained by a simple production method which is inexpensive, can be carried out quickly and is robust since it is not sensitive to variations of the formulation used.

DISCLOSURE OF THE INVENTION

[Definitions]

Within the meaning of this document, the term "nano-emulsion" means a composition having at least two phases, generally an oily phase and an aqueous phase, in which the average size of the dispersed phase is less than 1 micron, preferably 10 to 500 nm and in particular 20 to 100 nm, and most preferably 20 to 70 nm (see article C. Solans, P. Izquierdo, J. Nolla, N. Azemar and M. J. Garcia-Celma, Curr Opin Colloid In, 2005, 10, 102-110).

Within the meaning of this document, the term "lipid" denotes all the fats and oils or substances containing fatty acids present in animal fats and in plant oils. They are hydrophobic or amphiphilic molecules mainly formed of carbon, hydrogen and oxygen and having a density lower than that of water. The lipids can be in a solid state at room temperature (25° C.), as in waxes, or liquid as in oils.

The term "phospholipid" refers to lipids having a phosphate group, in particular phosphoglycerides. Most often, phospholipids comprise a hydrophilic end formed by the optionally substituted phosphate group and two hydrophobic ends formed by fatty acid chains. Particular phospholipids include phosphatidylcholine, phosphatidylethanolamine, phosphatidylinositol, phosphatidylserine and sphingomyelin.

The term "lecithin" refers to phosphatidylcholine, i.e. a lipid formed from a choline, a phosphate, a glycerol and two fatty acids. More broadly, it includes phospholipids extracted from living sources, of plant or animal origin, as long as they primarily consist of phosphatidylcholine. These lecithins generally consist of mixtures of lecithins carrying different fatty acids.

The term "fatty acids" refers to aliphatic carboxylic acids having a carbon chain of at least 4 carbon atoms. Natural fatty acids have a carbon chain of 4 to 28 carbon atoms (generally an even number). Long chain fatty acids are those between 14 and 22 carbon atoms long and very long chain fatty acids are those having more than 22 carbon atoms.

The term "surfactant" means compounds having an amphiphilic structure which gives them a specific affinity for oil/water-type and water/oil-type interfaces which enables them to reduce the free energy of these interfaces and to stabilise the dispersed systems.

The term "cosurfactant" means a surfactant acting with another surfactant to further reduce the energy of the interface.

The term "biological ligand" means any molecule which recognises, in a specific manner, a receptor generally arranged at the surface of the cells.

The term "nanocrystal" means a monocrystal of which at least one dimension is less than 100 nm. Nanocrystals which are currently available are usually inorganic materials; however organic nanocrystals may also be involved. The nanocrystals may be formed by pure substances or by compounds. In particular, they may also be metals or metal oxides. Nanocrystals may be conductors or semiconductors. In the case of semiconductor materials, reference is often also made to quantum particles (or quantum dots or even qdots). Owing to its small size, the nanocrystal behaves like a potential well which confines the electrons in three dimensions in a region of which the size corresponds to the de Broglie wavelength of the electrons, that is to say a few nanometers in a semiconductor. Owing to this confinement, the electrons of the nanocrystal have discrete, quantified energy levels which can be controlled by changing the size and shape of the nanocrystal.

[Emulsion]

According to a first aspect, the invention relates to a specific formulation of nanocrystals in the form of a nano-emulsion.

The emulsion is an oil-in-water type emulsion. The emulsion may be single or multiple, in particular by comprising a second aqueous phase in the dispersed phase.

Given their generally lipophilic affinity, the nanocrystals are encapsulated by the oily dispersed phase of the nano-emulsion.

As mentioned above, nanocrystals which are currently beneficial for applications within the fields of biology and medicine are mainly inorganic nanocrystals.

In particular, the inorganic materials may be metals such as gold and silver, oxides such as iron oxide, in particular magnetite, maghemite, gadolinium oxide and hafnium oxide.

In particular, the invention relates to semiconductor nanocrystals, even more particularly luminescent nanocrystals, in particular fluorescent nanocrystals. In fact, fluorescent nanocrystals are very useful markers within the field of imaging.

The wavelength of the light absorbed and/or emitted by the luminescent semiconductor nanocrystals not only depends on the size of the nanocrystal, but also on the energy gap of the semiconductor nanocrystal. A compound of which the energy gap corresponds to the beneficial wavelength in the intended application, for example the visible wavelength or the wavelength close to infrared, is therefore selected.

Examples of beneficial semiconductors for nanocrystals are, in particular CdS, CdSe, CdTe, InP, PbS, Si, CuInS and InGa semiconductors. The materials may be present in pure form or in a mixture, in doped form, or in nanocrystal of the core/shell type form, in which the nanocrystal core is coated with a shell, for example made of ZnS.

They may also be synthesised by different methods (by way of an organometallic, radiolytic, hydrothermal, co-precipitation, thermal decomposition or sol-gel process, etc) and are also commercially available.

Commercially available nanocrystals are generally stabilised by a layer of ligands carrying at least one hydrophobic chain, preferably a C8 (or more) hydrocarbon chain. These hydrophobic chain ligands may be, for example, fatty acids, thiols, phosphines, phosphine oxides, phosphates, phosphonates, or amines with a fatty chain. They may comprise one or more functional groups enabling them to bind to the nanocrystal, (for example lipoic acid, oligomeric phosphines, etc.). An example of the ligands used is, in particular, trioctylphosphine oxide (TOPO) having three C8 hydrocarbon chains. Alternatively, ligands having a single hydrophobic fatty chain which is generally longer, for example a C14 to C22 chain, in particular a C16 or C18 chain, may also be used.

The size of the nanocrystals able to be encapsulated in the nano-emulsion according to the invention is not particularly limited and is selected as a function of commercial availability and other application constraints. Typically, the nanocrystals have an average diameter of approximately 1 nm to 100 nm, preferably from 2 nm to 20 nm.

Owing to the use of a solubilising lipid in the dispersed phase, which makes it possible to increase the concentration of amphiphilic lipid, the proposed nano-emulsion makes it possible to encapsulate an increased concentration of nanocrystals.

It is thus possible to obtain a nano-emulsion encapsulating a plurality of identical or different nanocrystals within the same nanodroplet. The encapsulation of different nanocrystals makes it possible to provide multi-functional nano-emulsions. Therefore, the encapsulation of luminescent semiconductor nanocrystals which emit light in various quantities and at different wavelengths makes it possible to provide a nanoparticle having an optical "barcode".

The desired concentration of nanocrystals generally depends on the intended application. Typically, the oily phase contains 0.1 to 20 nmol/g of nanocrystals for a final concentration in the emulsion between, for example, 0.001 and 2 nmol/g.

The nanocrystals stabilised by the layer of hydrophobic ligands and dispersed in an organic solvent may be incorporated into the oily phase of the emulsion, the organic solvent then being evaporated. The organic solvents used may be, for example, methanol, ethanol, chloroform, dichloromethane, hexane, cyclohexane, DMSO, or DMF. So as to avoid any trace of toxic solvent, the nanocrystals may first be transferred into a solvent which is better tolerated, such as hexane.

The oily phase of the nano-emulsion also comprises at least one amphiphilic lipid and at least one solubilising lipid.

So as to form a stable nano-emulsion, it is generally necessary to include in the composition at least one amphiphilic lipid as a surfactant. The amphiphilic nature of the surfactant makes the oil droplets stable within the aqueous continuous phase.

The amphiphilic lipids comprise a hydrophilic part and a lipophilic part. They are generally selected from compounds of which the lipophilic part comprises a linear or branched saturated or unsaturated chain having 8 to 30 carbon atoms. They may be selected from phospholipids, cholesterols, lysolipids, sphingomyelins, tocopherols, glucolipids, stearylamines and cardiolipins, and may be of natural or synthetic origin; molecules formed of a fatty acid coupled to a hydrophilic group by an ether or ester function, such as sorbitan esters, for example sorbitan monooleate and sorbitan monolaurate sold under the Span® trade names by Sigma; polymerised lipids; lipids conjugated to short chains of polyethylene oxide (PEG), such as the non-ionic surfactants sold under the trade names Tween® by ICI Americas, Inc. and Triton® by Union Carbide Corp.; sugar esters such as sucrose monolaurate and sucrose dilaurate, sucrose monopalmitate and sucrose dipalmitate, sucrose monostearate and sucrose distearate; it being possible to use said surfactants alone or in a mixture.

Lecithin is the preferred amphiphilic lipid.

In one specific embodiment, all or part of the amphiphilic lipid may have a reactive function, such as a maleimide, thiol, amine, ester, oxyamine or aldehyde group. The presence of reactive functions allows functional compounds to graft at the interface. The reactive amphiphilic lipid is incorporated into the layer formed at the interface stabilising the dispersed phase, where it is liable to couple to a reactive compound present in the aqueous phase for example.

Generally, the oily phase will comprise 0.01 to 99% by weight, preferably 5 to 75% by weight, in particular 20 to 60% by weight and most particularly 33 to 45% by weight amphiphilic lipid.

The amount of amphiphilic lipid advantageously helps to control the size of the dispersed phase of the nano-emulsion obtained.

The emulsion according to the invention also comprises a solubilising lipid. The main task of this compound is to solubilise the amphiphilic lipid, which is poorly soluble, in the oily phase of the nano-emulsion.

The solubilising lipid is a lipid having a sufficient affinity for the amphiphilic lipid to allow it to be solubilised. The solubilising lipid is preferably solid at room temperature.

In the case where the amphiphilic lipid is a phospholipid, possible solubilising lipids are, in particular, glycerol derivatives, especially glycerides obtained by esterifying glycerol with fatty acids.

The solubilising lipid used is advantageously selected in dependence on the amphiphilic lipid used. It will generally have a similar chemical structure so as to bring about the desired solubilisation. It may be an oil or a wax. The solubilising lipid is preferably solid at room temperature (20° C.), but liquid at body temperature (37° C.).

The preferred solubilising lipids, in particular for phospholipids, are fatty acid glycerides, in particular saturated fatty acid glycerides, and in particular saturated fatty acid glycerides comprising 8 to 18 carbon atoms, even more preferably 12 to 18 carbon atoms. Advantageously, a mixture of different glycerides is involved.

Preferably, saturated fatty acid glycerides comprising at least 10% by weight C12 fatty acids, at least 5% by weight C14 fatty acids, at least 5% by weight C16 fatty acids and at least 5% by weight C18 fatty acids are involved.

Preferably, saturated fatty acid glycerides comprising 0% to 20% by weight C8 fatty acids, 0% to 20% by weight C10 fatty acids, 10% to 70% by weight C12 fatty acids, 5% to 30% by weight C14 fatty acids, 5% to 30% by weight C16 fatty acids and 5% to 30% by weight C18 fatty acids are involved.

The semi-synthetic glyceride mixtures sold by Gattefossé under the trade name Suppocire® NC, which are solid at room temperature and have been approved for human injection, are particularly preferred. The type N Suppocire® glycerides are obtained by direct esterification of fatty acids and glycerol. These are semi-synthetic glycerides of C8 to C18 saturated fatty acids, of which the quali-quantitative composition is shown in the table below.

The aforementioned solubilising lipids make it possible to obtain a formulation in the form of a nano-emulsion which is advantageously stable. Without wanting to draw on a specific theory, it is assumed that the aforementioned solubilising lipids make it possible to obtain droplets in the nano-emulsion having an amorphous core. The core thus obtained has an increased inner viscosity without exhibiting crystallinity. Crystallisation has an adverse effect on the stability of the nano-emulsion since it generally causes the droplets to aggregate and/or causes the encapsulated molecules to be expelled from the droplets. These properties thus promote the physical stability of the nano-emulsion and the stability of the encapsulation of nanocrystals over time.

The amount of solubilising lipid may vary widely as a function of the type and amount of amphiphilic lipid present in the oily phase. Generally, the oily phase will comprise 1 to 99% by weight, preferably 5 to 80% by weight and in particular 40 to 75% by weight solubilising lipid.

TABLE 1

| Fatty acid composition of Suppocire NC ® from Gattefossé | |
|---|---|
| Chain length | [% by weight] |
| C8 | 0.1 to 0.9 |
| C10 | 0.1 to 0.9 |
| C12 | 25 to 50 |
| C14 | 10 to 24.9 |
| C16 | 10 to 24.9 |
| C18 | 10 to 24.9 |

The oily phase may further comprise one or more other oils.

The oils used preferably have a hydrophilic-lipophilic balance (HLB) of less than 8 and even more preferably of between 3 and 6. Advantageously, the oils are used without any chemical or physical modification in advance of the formation of the emulsion.

In the proposed applications, the oils may be selected from biocompatible oils, in particular from oils of natural (plant or animal) or synthetic origin. Oils of this type include, in particular, oils of natural plant origin, including in particular soybean, linseed, palm, peanut, olive, grape seed and sunflower oils; and synthetic oils, including in particular triglycerides, diglycerides and monoglycerides. These oils may be in their natural form, refined or interesterified.

The preferred oils are soybean oil and linseed oil.

Generally, if present, the oil is contained in the oily phase in an amount ranging from 1 to 80% by weight, preferably between 5 and 50% by weight and in particular from 10 to 30% by weight.

The oily phase may further contain other additives, such as colourings, stabilisers, preservatives, fluorophores, contrast agents for imaging or other active ingredients in an appropriate amount.

The oily phase for the dispersed phase of the emulsion may be prepared by simply mixing the constituents, heating them if necessary until all the constituents have melted.

The aqueous phase used in the method according to the invention preferably consists of water and/or a buffer, such as a phosphate buffer, for example PBS ("phosphate buffer saline") or another saline solution, in particular sodium chloride.

Moreover, it comprises other ingredients, including a cosurfactant. The cosurfactant stabilises the nano-emulsion.

The cosurfactant may also have other effects in the intended application of the nano-emulsion. In particular, it may be grafted so as to carry a targeting ligand.

The cosurfactants which may be used in emulsions according to the present invention are preferably water-soluble surfactants. The water-soluble surfactants are preferably alkoxylated and preferably comprise at least one chain composed of ethylene oxide units (PEO or PEG) or ethylene oxide and propylene oxide units. Preferably, the number of units in the chain varies between 2 and 500.

Examples of cosurfactants include, in particular, the conjugated compounds polyethylene glycol/phosphatidylethanolamine (PEG-PE), fatty acid and polyethylene glycol ethers such as the products sold under the Brij® trade names (for example Brij® 35, 58, 78 or 98) by ICI Americas Inc., fatty acid and polyethylene glycol esters such as the products sold under the Myrj® trade names by ICI Americas Inc. (for example Myrj® 45, 52, 53 or 59) and ethylene oxide and propylene oxide block copolymers such as the products sold under the Pluronic® trade names by BASF AG (for example Pluronic® F68, F127, L64, L61, 10R4, 17R2, 17R4, 25R2 or 25R4) or the products sold under the Synperonic® trade name by Unichema Chemie BV (for example Synperonic® PE/F68, PE/L61 or PE/L64).

The aqueous phase preferably comprises 2 to 50% by weight, preferably 5 to 30% by weight and in particular 10 to 20% by weight of a cosurfactant.

In a preferred embodiment, the continuous phase also comprises a thickening agent such as a glycerol, a saccharide, oligosaccharide or polysaccharide, a gum or even a protein, preferably glycerol. In fact, the use of a continuous phase of a higher viscosity facilitates emulsification and thus allows the sonication time to be reduced.

The aqueous phase advantageously comprises 0 to 50% by weight, preferably 1 to 30% by weight and in particular 5 to 20% by weight of a thickening agent.

Naturally, the aqueous phase may further comprise other additives such as colourings, stabilisers and preservatives in appropriate amounts.

The aqueous phase for the continuous phase of the emulsion may be prepared by simply mixing the different constituents with the selected aqueous medium.

The absolute value of the zeta potential of the dispersed phase is preferably lower than 20 mV, that is to say between −20 and 20 mV. In fact, an increased absolute value of the zeta potential of the nanoparticles leads to their accumulation in the body, in particular in the liver, the spleen, the lungs and also in the kidneys. However, for applications within the field of imaging, the opposite is sought—a stealthy formulation which has a long plasmatic life after intravenous injection.

[Preparation Method]

The nano-emulsion described above may be prepared easily by dispersing suitable amounts of oily phase and aqueous phase under the effect of a shear force.

In the method according to the invention, the different oily constituents and the inorganic nanocrystals are initially mixed to prepare an oily premix for the dispersed phase of the emulsion. The mixing may optionally be facilitated by placing one of the constituents or the complete mixture in solution in an appropriate organic solvent. The organic solvent is then evaporated so as to obtain a homogeneous oily premix for the dispersed phase.

Furthermore, it is preferred to produce the premix at a temperature at which all of the ingredients are liquid.

According to a preferred embodiment, the dispersed phase of the nano-emulsion is grafted at the surface with beneficial molecules, such as biological ligands. A grafting process of this type makes it possible to recognise specific cells (for example tumour cells as described, for example, in the article by S. Achilefu, Technology in Cancer Research & Treatment, 2004, 3, 393-408) or specific body organs.

The surface grafting process is preferably achieved by coupling molecules or their precursors with an amphiphilic compound, in particular with the cosurfactant. In this case, the amphiphilic compound acts as a spacer enabling the targeting molecules to be arranged at the surface. This coupling may be carried out before or after emulsification. The latter case may be preferred when the chemical reactions used are compatible with the colloidal stability of the emulsions, in particular with regard to pH. The pH during the coupling reaction is preferably between 5 and 11.

The beneficial molecules may be, for example:
biological targeting ligands, such as antibodies, peptides, saccharides, aptamers, oligonucleotides or compounds, such as folic acid;
a stealth agent: a substance added so as to make the nano-emulsion invisible to the immune system, to increase its circulation time within the organism and to slow down its elimination.

It is also possible to introduce inside the nanoparticles, at the surface thereof or adsorbed thereon, by way of a covalent bond or not:
imaging agents, in particular for MRI (magnetic resonance imaging), PET (positron emission tomography), SPECT (single photon emission computed tomography), ultrasonography, radiography, X-tomography and optical imaging (fluorescence, bioluminescence, diffusion, etc.); and/or
therapeutic agents.

The proportion of oily phase and aqueous phase is highly variable. However, usually, the nano-emulsions will be prepared with 1 to 50%, preferably 5 to 40%, and in particular 10 to 30% by weight oily phase and 50 to 99%, preferably 60 to 95% and in particular 70 to 90% by weight aqueous phase.

Advantageously, the oily phase is dispersed in the aqueous phase in a liquid state. If one of the phases solidifies at room temperature, it is preferable to make the mixture with one, or preferably the two phases heated to a temperature greater than or equal to the melting temperature.

The emulsification under shear force effect is preferably produced using a sonicator or a microfluidiser. Preferably, the aqueous phase and then the oily phase are introduced into an appropriate cylindrical receptacle in the desired proportions and the sonicator is dipped into the medium and switched on for long enough to obtain a nano-emulsion, usually a few minutes.

This produces a homogeneous nano-emulsion in which the average diameter of the oil droplets is greater than 10 nm and less than 200 nm, preferably from 20 to 50 nm.

Before conditioning, the emulsion may be diluted and/or sterilised, for example by filtration or by dialysis. This step makes it possible to eliminate any aggregates which might have formed during preparation of the emulsion.

The emulsion thus obtained is ready to use, after dilution if necessary.

[Methods of Use]

The formulation according to the invention may be used as it stands or adapted to the intended application, for example by way of dilution, for administration of the nanocrystal(s) to humans or animals.

Owing to the fact that it may be prepared exclusively from constituents approved for humans, the formulation is particularly suitable for parenteral administration. However, it is also possible for administration to be achieved by other routes, in particular orally or topically.

The formulation disclosed thus enables a formulation to be obtained which is useful in the administration of nanocrystals for applications within the fields of biology and medicine, in particular within the field of medical imaging.

The present invention also relates to a method of phototherapeutic or thermotherapeutic treatment, comprising administration of an effective therapeutic amount of the formulation as defined above to a mammal, preferably a human, in need thereof and to a diagnostic method comprising administration of the aforementioned formulation to a mammal, preferably a human.

BRIEF DESCRIPTION OF THE DRAWINGS

The invention will be described in greater detail hereinafter by way of the Examples below and figures, in which.

EXAMPLES

Example 1

Figure 1:
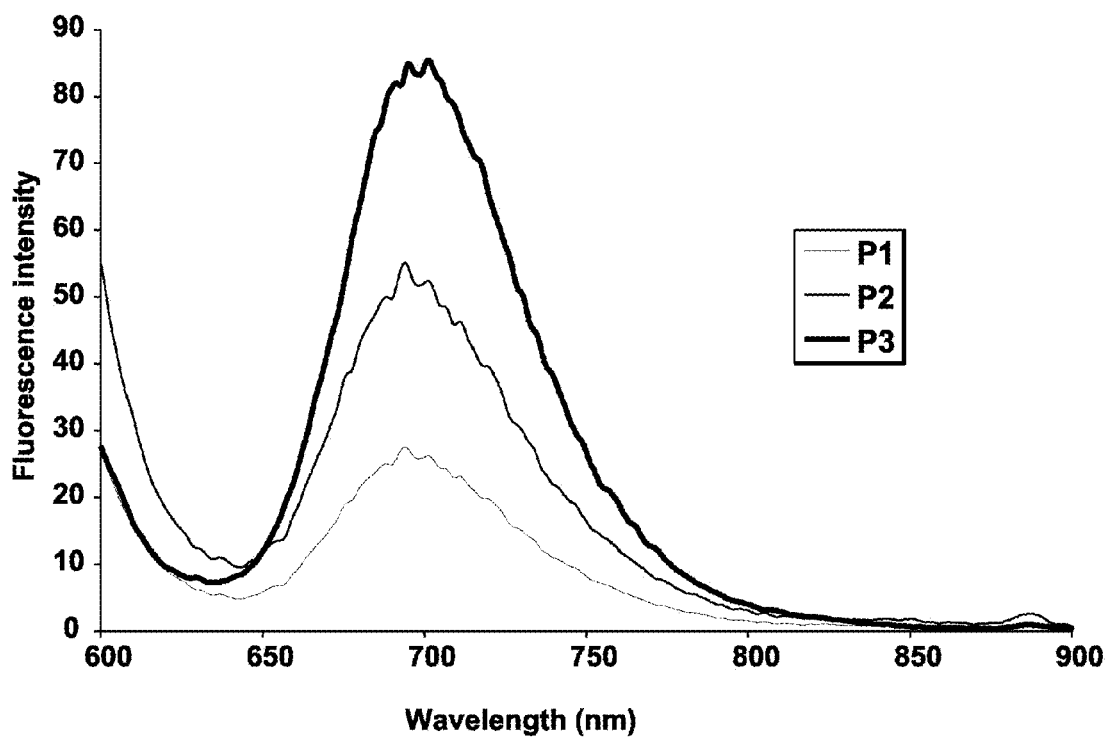
FIG. 1: shows the fluorescence spectra of nano-emulsions P1, P2 and P3 diluted 10 times in PBS.

Preparation of Nano-Emulsions Encapsulating Fluorescent Semiconductor Nanocrystals 1) Preparation of the Premix of the Dispersed Phase A batch of 1 g of premix was prepared in the following manner. 50 mg of soybean oil (Sigma-Aldrich), 450 mg of semi-synthetic glycerides (sold under the trade name Suppocire® NC by Gattefossé) and 400 mg soy lecithin (enriched with 75% phosphatidylcholine, sold by Lipoïd under the trade name Lipoïd® S75) were placed in an appropriate receptacle. These compounds were dissolved in chloroform, then evaporated at low pressure. The remaining mixture was dried at 50° C. so as to obtain a premix in the form of a viscous oil which solidifies upon cooling.

2) Preparation of Fluorescent Semiconductor Nanocrystals

The CdTe—ZnS-based core/shell nanocrystals emitting light within the close infrared range (705 nm) and having an average diameter of 10±2 nm (Qdots 705 ITK Organic sold by Invitrogen under reference Q21761MP), sold in 1 µM solution in decane were transferred into a hexane solution as follows. Four volumes (4×) of a methanol/isopropanol solution (volume ratio 75:25) were added to one volume (1×) of semiconductor nanocrystals. The mixture obtained was mixed by vortex then centrifuged for 5 minutes at 3000 rpm. The supernatant was then removed and the semiconductor nanocrystals were redispersed in one volume (1×) of hexane.

3) Preparation of the Dispersed Phase

At a temperature of approximately 70° C., 0.334 g of the premix prepared above in the previous step was recovered and 0 µL (P0), 125 µL (0.125 nmols) (P1), 250 µL (0.250 nmols) (P2) et 500 µL (0.500 nmols) (P3) of the dispersion of semiconductor nanocrystals obtained as described above were added thereto. The solvent was then evaporated at low pressure and the mixture obtained was dried at 50° C. so as to obtain a viscous oil which solidifies upon cooling. The solution was homogenised by vortex and kept at 70° C. before the emulsification phase.

4) Preparation of the Continuous Phase

A batch of 1.666 g of continuous phase was prepared as follows. The continuous phase was formed of 0.050 g of glycerol, 0.228 g of polyoxyethylene stearate with 50 mols ethylene oxide (sold under the trade name Myrj® 53 by ICI Americas Inc.) and a phosphate buffer solution (PBS) to make the mixture up to 1.666 g. This solution was heated to 50° C. before emulsification.

TABLE 2

Composition of the formulation of Example 1

|  | Constituents | Weight (mg) |
| --- | --- | --- |
| Dispersed phase | Suppocire NC | 150 |
|  | Soybean oil | 50 |
| Continuous phase | Saline solution | 1389 |
|  | Glycerol | 50 |
| Surfactants | Lecithin | 133 |
| Dopant | Myrj 53 | 228 |
|  | CdTe—ZnS nanocrystals | 0; 0.125; 0.250 and 0.500 nmols |

5) Emulsification

The batch of continuous phase obtained above was added to 0.334 g of the batch of dispersed phase obtained under point 3 and a mixture of composition as indicated in Table 2 above was obtained. The mixture was emulsified using an AV505® sonicator fitted with a conical probe measuring 3 mm in diameter (Sonics Newtown) for 5 minutes with a total energy of 6000 joules. Nano-emulsions (P0), (P1), (P2) and (P3) were obtained which were very stable and were clear, their colouration increasing with the concentration of nanocrystals.

6) Characteristics

The average diameter of the dispersed phase of the nano-emulsions obtained, determined from samples diluted at a ratio of 1:1000 in 0.1 M PBS using a Zetasizer (Malvern Instruments), was 30±10 nm.

The zeta potential of the prepared nano-emulsions, determined using the same instrument, was −8.6±7.7 mV. The nano-emulsions prepared exhibited excellent colloidal stability (>3 months).

The fluorescence spectra of the prepared nano-emulsions, recorded using a spectrofluorometer (PERKIN ELMER model LS 50), revealed beneficial optical properties, even after encapsulation.

Example 2

Use of a Nano-Emulsion Encapsulating Fluorescent Semiconductor Nanocrystals for Fluorescence Imaging A batch of 100 µL of nano-emulsion (P3) prepared in accordance with Example 1 was diluted twice by adding 100 µL of a phosphate buffer solution. The batch of 200 µL (0.025 nM of nanocrystals) obtained was then injected intravenously (caudal vein) into the tail of female nude mice aged between 6 and 8 weeks and kept under pathogen-free conditions (IFFA-Credo, Marcy l'Etoile, France).

The mice, kept under general anaesthetic by way of gas (isofluorane) throughout the procedure, were imaged using a fluorescence reflectance imaging device (FRI) comprising a crown of LEDs as an excitation source fitted with interference filters, emitting light at 633 nm (illumination power 50 µW·cm⁻²). The device is described in greater detail in the article by Texier, I. et al., "Luminescent probes for optical in vivo imaging", Proceedings of the SPIE, 2005, 5704, 16-22. The images were collected after filtration by means of a RG665 coloured filter of optical density >5 at the excitation wavelength by a CCD camera (Orca BTL, Hamamatsu) with an exposure time of 500 ms. The signals were quantified using image processing software.

Figure 2:
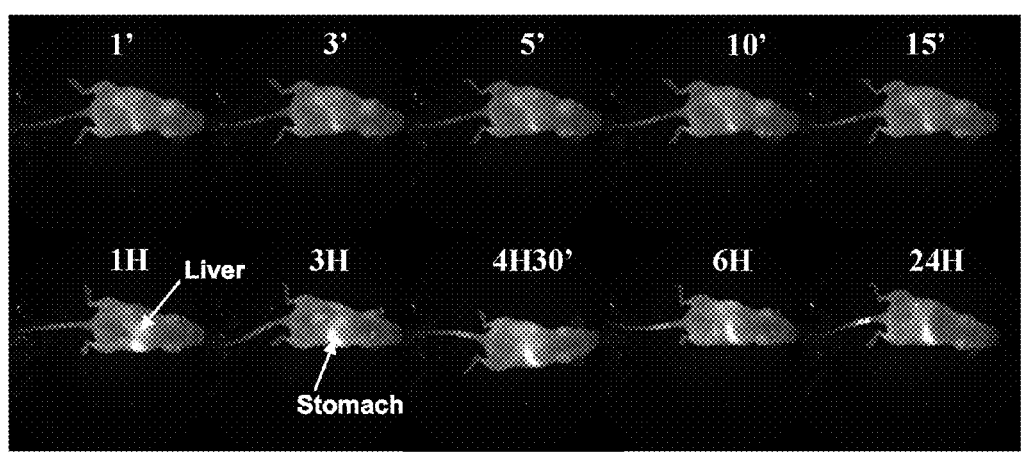
FIG. 2: shows fluorescence reflectance images of healthy nude mice having received an injection of nanocrystal nano-emulsion (P3) as described in Example 2 over time.

FIG. 2 shows the images obtained and reveals the biodistribution of nano-emulsion (P3) in the mice during the 24 hours following injection of the nano-emulsion. It can be seen that the mouse is illuminated with a homogenous distribution of the nanocrystals throughout the body for the first 15 minutes after injection. After one hour, the signal is clearly concentrated in the stomach and this reduces over time. There is a small accumulation in the liver which indicates a good level of stealth of the emulsion after injection.

Figure 3:
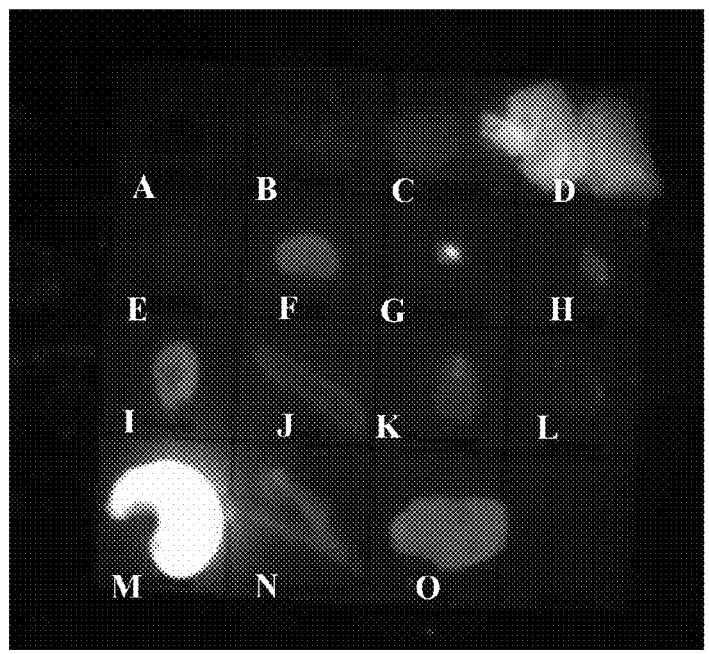
FIG. 3: shows fluorescence reflectance images of the organs of a mouse having received treatment in accordance with Example 2 and killed 24 hours later (heart (A), lung (B), brain (C), skin (D), muscle (E), kidney (F), adrenal gland (G), bladder (H), intestine (I), spleen (J), pancreas (K), fat (L), stomach (M) and uterus-ovary (N)
Figure 4:
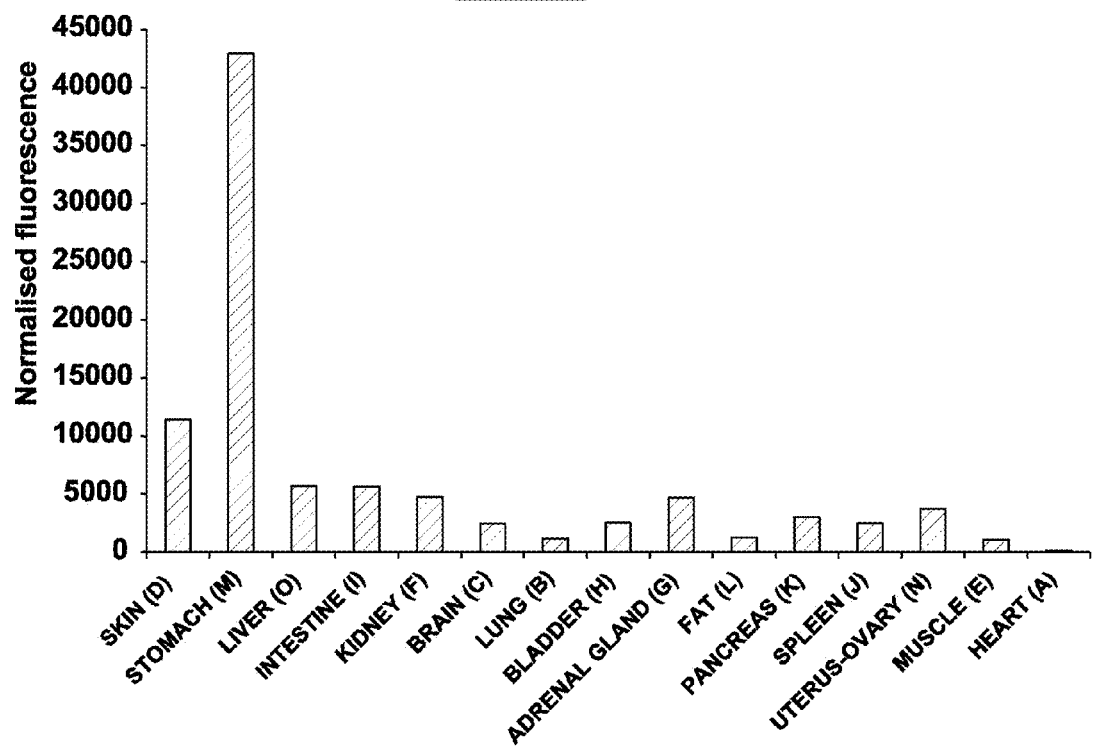
FIG. 4: shows a bar chart of the fluorescence in said organs of the mouse having received treatment in accordance with Example 2 and killed 24 hours later.

FIG. 3 shows the images of the organs of the mouse killed 24 hours after injection, said images being obtained using the fluorescence reflectance imaging device. It can be seen that the signal observed in the liver, spleen, lungs and kidneys is very weak compared to the signal observed in the stomach, skin and adrenal gland.

These results highlight a plasmatic life after intravenous injection of at least 1 hour and therefore a stealthy character of the nano-emulsions according to the invention. Plasmatic life is a significant parameter when selecting formulations which can be used within the fields of biology and medicine, and in particular within the fields of medical imaging, thermotherapy and phototherapy.

Example 3

Highlighting Stability of the Nano-Emulsion

The experiments below were carried out in order to demonstrate the stability conferred to the nano-emulsions by the solubilising lipid.

Example 3a

Highlighting the High Inner Viscosity of the Droplets by Way of NMR

A nano-emulsion comprising 255 mg of Suppocire® NC (Gattefossé) (solubilising lipid), 85 mg of soybean oil (Sigma Aldrich) (oil), 345 mg of Myrj52® (ICI Americas Inc) (cosurfactant), 65 mg of Lipoid® s75 (lecithin, amphiphilic lipid) and a phosphate buffer (PBS) was prepared in accordance with the protocol of Example 1.

Figure 5:
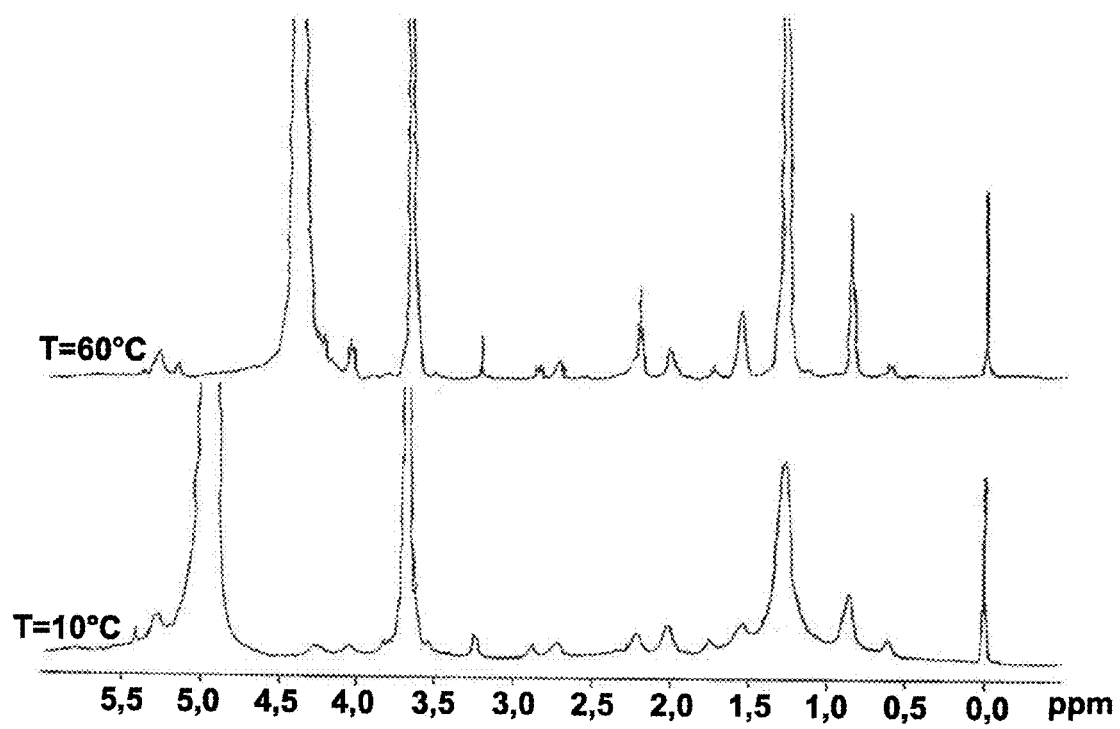
FIG. 5: shows two ¹H NMR spectra of the nano-emulsions after production for temperatures T=10° C. and T=60° C. (Example 3).

The nano-emulsion was analysed at 10° C. and at 60° C. by nuclear magnetic resonance of the proton. The peaks associated with the core components of the droplets of the nano-emulsion (oil/solubilising lipid and amphiphilic lipid) (0.9; 1.5; 1.6; 2.0; 2.2; 4.1; 4.2 ppm) observed within the $^1$H NMR spectra were enlarged compared with the reference (0 ppm 4,4-dimethyl-4-silapentane-1-sulphonic acid (DSS)), especially when the temperature was low, thus highlighting the high inner viscosity of the droplets. The peaks associated with the cosurfactant Myrj53® (3.7 ppm) did not exhibit any enlargement which indicates that the cosurfactant remained at the surface of the droplets, the polyoxyethylene chains being solubilised in the aqueous buffer (FIG. 5).

Example 3b

Highlighting the Absence of Crystallisation in the Droplets by Way of Differential Scanning Calorimetry A nano-emulsion comprising 150 mg of Suppocire® NC (Gattefossé) (solubilising lipid), 50 mg of soybean oil (Sigma Aldrich) (oil), 228 mg of Myrj53® (ICI Americas Inc) (cosurfactant), 100 mg of Lipoid® s75 (lecithin, amphiphilic lipid) and a phosphate buffer (PBS) was prepared in accordance with the protocol of Example 1.

Figure 6:
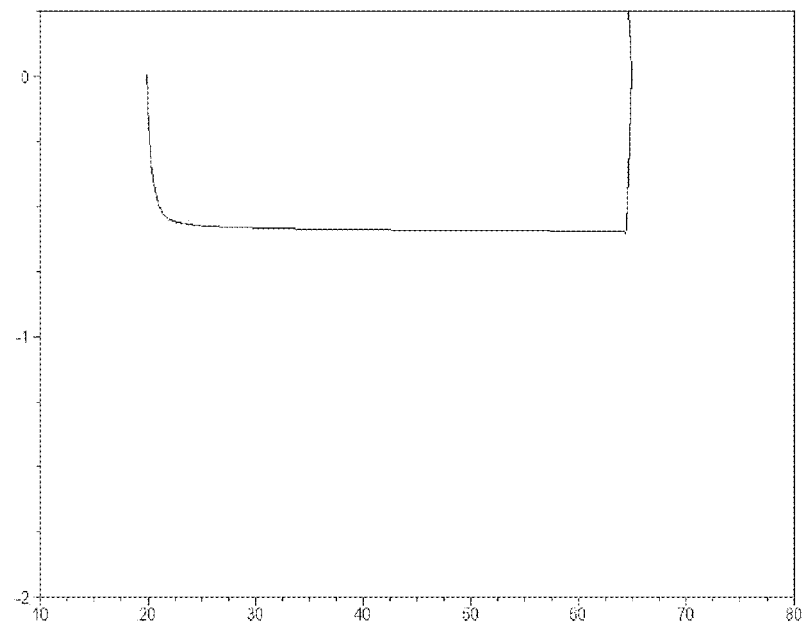
FIG. 6: shows thermograms (heat flow (W/g) as a function of temperature in ° C.) obtained by differential scanning calorimetry (DSC) of the nano-emulsions after production (a) and after 4 months of storage at room temperature (b) using a Universal V3.8B TA instrument (Example 3).
Figure 6:
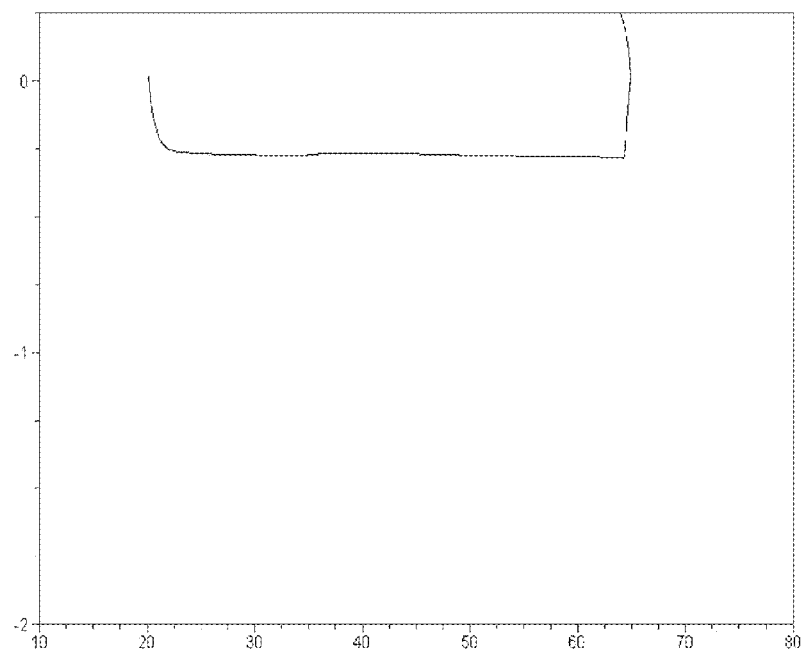

The thermograms obtained by differential scanning calorimetry analysis of the nano-emulsion after preparation and after 4 months of storage at room temperature show that no fusion peak was observed after production, nor after storage at room temperature over 4 months, which indicates that the droplets were not crystallised (FIG. 6).

Example 3c

Revealing the Influence of the Composition of Nano-Emulsions on their Physical Stability Three nano-emulsions comprising 228 mg of Myrj53® (ICI Americas Inc) (co-surfactant), 100 mg of Lipoid® s75 (lecithin, amphiphilic lipid), 1600 μL of phosphate buffer (PBS), Suppocire® NC (Gattefossé) (solubilising lipid) and soybean oil (Sigma Aldrich) (oil) in the amounts indicated in Table 3 were prepared in accordance with the protocol of Example 1.

TABLE 3

| Amounts of Suppocire ® NC and soybean oil in the nano-emulsions | | | |
| --- | --- | --- | --- |
| Nano-emulsion | NC0 | NC50 | NC100 |
| Suppocire ® NC | 0 | 100 mg | 200 mg |
| Soybean oil | 200 mg | 100 mg | 0 |

Figure 7:
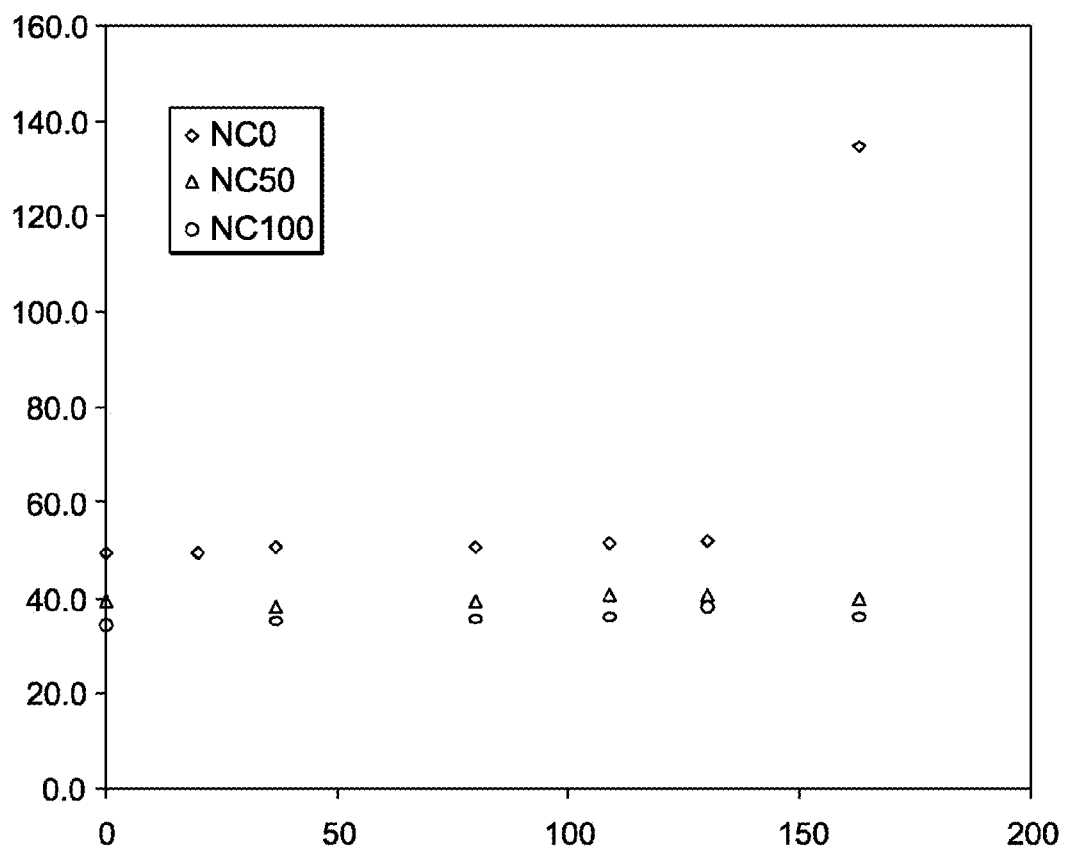
FIG. 7: shows the development of the size of the droplets (in nm) of the nano-emulsion as a function of time (in days) for three nano-emulsions at 40° C. The diamonds represent a nano-emulsion containing no solubilising lipid and comprising oil, the triangles represent a nano-emulsion comprising a 50:50 mixture of solubilising lipid and oil and the circles represent a nano-emulsion containing no oil and containing solubilising lipid (Example 3).

A test of accelerated stability at 40° C. was carried out on the three nano-emulsions obtained. Monitoring the size/polydispersity of the nano-emulsions over time made it possible to highlight the stabilising effect of the solubilising lipid. Whereas the size of the nano-emulsions containing no solubilising lipid increased considerably after almost 170 days at 40° C., the nano-emulsions containing solubilising lipid exhibited no significant change in droplet size (FIG. 7). The results show that adding solubilising lipid to the composition of the nano-emulsions confers better physical stability to the droplets and to the nano-emulsion.

The invention claimed is:
1. A formulation of metal, metal oxide or semi-conductor nanocrystals in the form of a nano-emulsion, comprising a continuous aqueous phase and at least one dispersed oily phase encapsulating the nanocrystals, wherein a surface of the dispersed oily phase has a zeta potential having an absolute value lower than 20 mV,
    wherein the oily phase comprises:
        at least one phospholipid, and
        at least one solubilising lipid consisting of a mixture of saturated fatty acids glycerides comprising:
            at least 10% by weight C12 fatty acids,
            at least 5% by weight C14 fatty acids,
            at least 5% by weight C16 fatty acids and
            at least 5% by weight C18 fatty acids,
    wherein the aqueous phase comprises a cosurfactant, and
    wherein the cosurfactant comprises at least one chain formed of ethylene oxide units or ethylene oxide and propylene oxide units.
2. The nanocrystal formulation according to claim 1, wherein the nanocrystals are luminescent.
3. The nanocrystal formulation according to claim 1, wherein the oily phase further comprises at least one oil.
4. The nanocrystal formulation according to claim 1, wherein the cosurfactant is selected from the group consisting of conjugated compounds polyethylene glycol/phosphatidylethanolamine (PEG/PE), fatty acid and polyethylene gly- col ethers and fatty acid and polyethylene glycol esters, and ethylene oxide and propylene oxide block copolymers.

5. The nanocrystal formulation according to claim 1, wherein the dispersed phase is functionalised with a beneficial molecule selected from the group consisting of a biological targeting ligand, a stealth agent, an imaging agent and a therapeutic agent.

6. The nanocrystal formulation according to claim 1, wherein the at least one solubilising lipid consisting of a mixture of saturated fatty acids glycerides comprises:
   from 0% to 20% by weight C8 fatty acids,
   from 0% to 20% by weight C10 fatty acids,
   from 10% to 70% by weight C12 fatty acids,
   from 5% to 30% by weight C14 fatty acids,
   from 5% to 30% by weight C16 fatty acids and
   from 5% to 30% by weight C18 fatty acids.

7. The nanocrystal formulation according to claim 1, wherein the oily phase further comprises at least one oil having a hydrophilic-lipophilic balance (HLB) of less than 8.

* * * * *